United States Patent [19]

Lunzer

[11] Patent Number: 4,503,225
[45] Date of Patent: Mar. 5, 1985

[54] PROCESS FOR THE PREPARATION OF FREE-FLOWING, COARSELY CRYSTALLINE SODIUM DICHLOROISOCYANURATE DIHYDRATE

[75] Inventor: Friedrich Lunzer, Ottensheim, Austria

[73] Assignee: Chemie Linz Aktiengesellschaft, Linz, Austria

[21] Appl. No.: 513,160

[22] Filed: Jul. 12, 1983

[30] Foreign Application Priority Data

Jul. 26, 1982 [DE] Fed. Rep. of Germany ....... 3227817

[51] Int. Cl.$^3$ ............................................ C07D 251/36
[52] U.S. Cl. .................................................... 544/190
[58] Field of Search ......................................... 544/190

[56] References Cited

U.S. PATENT DOCUMENTS

| | | | |
|---|---|---|---|
| 3,035,056 | 5/1962 | Symes | 260/248 |
| 3,035,057 | 5/1962 | Symes et al. | 260/248 |
| 3,818,004 | 6/1974 | Berkowitz | 544/190 |
| 3,888,855 | 6/1975 | Berkowitz | 544/190 |
| 4,182,871 | 1/1980 | Moller | 544/190 |
| 4,374,985 | 2/1983 | Doonan et al. | 544/190 |

FOREIGN PATENT DOCUMENTS

| | | |
|---|---|---|
| 1162378 | 2/1964 | Fed. Rep. of Germany . |
| 1178072 | 9/1964 | Fed. Rep. of Germany . |
| 1207393 | 12/1965 | Fed. Rep. of Germany . |
| 1670985 | 2/1972 | Fed. Rep. of Germany . |
| 2324356 | 11/1973 | Fed. Rep. of Germany . |
| 2433113 | 1/1975 | Fed. Rep. of Germany . |

*Primary Examiner*—John M. Ford
*Attorney, Agent, or Firm*—Wenderoth, Lind & Ponack

[57] ABSTRACT

Novel, advantageous process for the preparation of free-flowing, coarsely crystalline sodium dichloroisocyanurate dihydrate by reacting dichloroisocyanuric acid and sodium hydroxide, sodium carbonate or sodium bicarbonate in a reaction medium containing 20 to 30 parts by weight of water per 70 to 80 parts by weight of an organic, water-miscible solvent which is inert towards dichloroisocyanuric acid, and removing the organic solvent, together with the free water still present, by drying in vacuo at temperatures from room temperature to 50° C.

8 Claims, No Drawings

PROCESS FOR THE PREPARATION OF FREE-FLOWING, COARSELY CRYSTALLINE SODIUM DICHLOROISOCYANURATE DIHYDRATE

The present invention relates to a novel, advantageous process for the preparation of coarsely crystalline, free-flowing sodium dichloroisocyanurate dihydrate.

Sodium dichloroisocyanurate dihydrate can be represented by the following structural formula

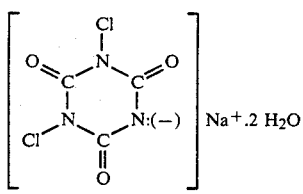

although neither the structural formula nor the name sodium dichloroisocyanurate dihydrate should represent a restriction to one of the tautomeric forms in which the salt can exist.

Sodium salts of dichloroisocyanuric acid are widely used as base substances for available chlorine in solid bleaches, sterilizing agents, disinfectants and cleaning agents, and, compared with conventional chlorine compounds, for example chloramine-T, 1,3-dichlor-5,5-dimethylhydantoin, lithiumhypochlorite or even trichloroisocyanuric acid, have the advantage that they are significantly more stable under ambient conditions and in the absence of substantial amounts of moisture. The sodium salts of dichloroisocyanuric acid can thus easily be stored, and release their active chlorine only when they are brought into an aqueous solution envisaged for a bleaching action or a sterilizing or disinfecting action.

Sodium dichloroisocyanurates occur in three different forms, that is to say in the anhydrous form, as the monohydrate with a water of hydration content of about 7.6% by weight, and as the dihydrate with a water of hydration content of about 14.1% by weight (in this context, compare U.S. Pat. No. 3,035,056 and U.S. Pat. No. 3,035,057).

The sodium salt of dichloroisocyanuric acid in the dihydrate form has the great advantage over the anhydrous form and the monohydrate and also over most other starting materials for active chlorine that it is neither ignitable nor inflammable. Expensive and troublesome safety measures can therefore be dispensed with in the manufacture, storage and dispatch of the abovementioned bleaches, sterilizing agents, cleaning agents and disinfectants.

According to a process described in U.S. Pat. No. 3,035,056, sodium dichloroisocyanurate dihydrate is prepared by treating trisodium isocyanurate with chlorine. A mixture of sodium dichloroisocyanurate and sodium chloride side by side in aqueous solution is formed in this reaction. However, the presence of sodium chloride in addition to sodium dichloroisocyanurate is undesirable, since the stability of the dihydrate salts is impaired by adhering sodium chloride. The reaction mixture is therefore diluted with large amounts of water to remove sodium chloride, but this means that considerable amounts of sodium dichloroisocyanurate also remain in the mother liquor. Because of the NaCl content, however, this mother liquor cannot be directly recycled again to the reaction and used again.

German Patent Specification No. 1,207,393 describes a process for the preparation of sodium dichloroisocyanurate and its monohydrate and dihydrate in which two equivalents of trichloroisocyanuric acid and one equivalent of trisodium cyanurate are reacted in an aqueous medium to a constant pH value of 5–7. Although no noticeable amounts of sodium chloride are formed as a by-product in this process, it is necessary additionally to prepare trichloroisocyanuric acid as the starting material.

Finally, it is known from German Offenlegungsschrift No. 2,324,356 that sodium dichloroisocyanurate dihydrate can be prepared by neutralizing dichloroisocyanuric acid with aqueous sodium hydroxide solution at a pH value of 6–7 and a temperature of 5° to 65° C. When the reaction has ended, at least 95% of the adhering water is removed by drying at 15° to 50° C., whereupon a product mixture of dihydrate, monohydrate and dichloroisocyanurate with a water content of about 11% by weight is obtained.

All the above processes are carried out in an aqueous medium, which means that considerable difficulties arise while separating off, purifying and drying the salts.

Sodium dichloroisocyanurate dihydrate is obtained from water in an extremely fine crystalline form with a very low cross-sectional area and is therefore difficult to remove from the mother liquor and wash out. After precipitation from the aqueous suspension, the dihydrate salt is in the form of a moist substance with an adhering water content of about 10 to 40% by weight, and must be dried under mild conditions. It proves difficult here to dry the sodium dichloroisocyanurate dihydrate such that it contains only negligible amounts of free water, without at the same time removing the loosely bonded water of hydration. In addition, at higher drying temperatures the content of active chlorine is decreased by decomposition and severe losses occur by sublimation. After drying, a product is obtained which is mostly in the form of dust and, in this form, has disadvantages during further processing and use as a bleach.

Furthermore, a saturated aqueous mother liquor containing about 10 to 25% by weight of dissolved sodium dichloroisocyanate in the range between 0° C. and about 40° C., depending on the temperature at which the preparation is carried out, is obtained in the known preparation variants. In an economically acceptable process, it is therefore necessary to improve the yield of sodium dichloroisocyanurate dihydrate by evaporating the mother liquor. However, during the evaporation hydrolysis products and decomposition products are formed in the mother liquor and impair the stability of the sodium dichloroisocyanurate dihydrate prepared.

To avoid these difficulties, German Auslegeschrift No. 2,433,113 described a drying process in which the sodium dichloroisocyanurate dihydrate is brought into contact again, after removal from the aqueous reaction medium, with a water-miscible organic solvent, for example acetone, and dried at a temperature of less than 40° C. in order to remove the organic solvent, together with the residual content of free water. Although a free-flowing product is obtained in this process, the disadvantage that the salt must first be separated off from the aqueous reaction medium and then mixed again with an organic solvent must be accepted.

The processes described in German Offenlegungsschrift No. 1,670,985, German Patent Specification No. 1,162,378 and German Auslegeschrift No. 1,178,072 for the preparation of chlorinated cyanuric acid or of salts thereof have the common factor that a surfactant substance is added either to the aqueous reaction medium or to the moist substance separated off. Although this addition gives, after drying, crystals having a higher cross-sectional area, it does not avoid the difficulties associated with drying the adhering water and the high content of sodium dichloroisocyanurate in the aqueous mother liquor.

The present invention is thus based on the object of providing an economical process which enables sodium dichloroisocyanurate dihydrate to be prepared in a coarsely crystalline form avoiding the disadvantages associated with the known processes and to be dried in a simple manner without removal of the water of hydration content, to give a free-flowing loose material.

It was now possible to find, surprisingly, that this object can be achieved, according to the invention, by neutralizing dichloroisocyanuric acid with a basic sodium compound in a reaction medium containing, in addition to an organic water-miscible solvent, a certain amount of water sufficient to form the dihydrate salt, the sodium dichloroisocyanurate dihydrate being obtained in a coarsely crystalline form which is easy to dry, providing a substantial technological and economical advance.

The present invention accordingly relates to a process for the preparation of coarsely crystalline, free-flowing sodium dichloroisocyanurate dihydrate, which comprises reacting dichloroisocyanuric acid with the equivalent amount of a base from the group of sodium hydroxide, sodium carbonate and sodium bicarbonate at temperatures from 0° C. to room temperature in a reaction medium which contains 20 to 30 parts by weight of water per 70 to 80 parts by weight of an organic, water-miscible solvent which is inert towards dichloroisocyanuric acid and is used in an amount such that at least 2 molar equivalents of water, based on the amount of dichloroisocyanuric acid employed, are present, and then separating off the sodium dichloroisocyanurate dihydrate, which is obtained in a coarsely crystalline form, and removing the solvent, together with free water still adhering, by drying in vacuo at room temperature to 50° C.

The process according to the invention can be carried out by dissolving or suspending the dichloroisocyanuric acid in the organic reaction medium with a water content of 20 to 30% by weight, and adding the equivalent amount of the basic sodium compound, with continuous stirring. However, it is also possible to dissolve the dichloroisocyanuric acid in the organic solvent and to react it, while stirring, with an aqueous solution of the basic sodium compound, the concentration of which is calculated such that the water content of the reaction mixture is 20 to 30 parts by weight, based on the amount of organic solvent, at the neutralization point.

In any case, sodium hydroxide is preferably added in the form of aqueous sodium hydroxide solution for neutralization of the dichloroisocyanuric acid. In calculating the concentration of aqueous NaOH, however, the water content of the organic solvent in which the dichloroisocyanuric acid is present should be taken into consideration, so that the water content is kept within 20 to 30 parts by weight at the neutralization point.

Within the abovementioned limits, particularly advantageous reaction conditions exist if the reaction according to the invention is carried out in the presence of 20 to 25 parts by weight of water, based on the amount of organic solvent. During the neutralization, the reaction temperature is preferably kept between 0° and 10° C., in particular between 0° and 5° C.

When the reaction is complete, which can take from one to several hours, depending on the nature of the basic sodium compound and the amount employed, the suspension containing sodium dichloroisocyanurate dihydrate is removed from the reaction vessel. The solid substances are separated off from the liquid phase of the reaction mixture by any known process for separating off solid substances from liquids, for example by filtration, centrifugation, decanting or the like, the dihydrate salt of dichloroisocyanurate acid being precipitated in an easily filterable, coarsely crystalline form containing only 5 to 8% by weight of residual moisture, based on the sodium dichloroisocyanurate, depending on the process variant and the amount of water in the organic solvent. The solid product, which is still moist from the organic solvent, is then dried to constant weight under a water pump vacuum for the purpose of obtaining stable, pure sodium dichloroisocyanurate dihydrate. Drying temperature below 50° C., preferably temperatures of 25° to 30° C., are thereby used, removal of the organic solvent, together with the small amount of free water, being extremely quick and simple to effect. Dry, free-flowing crystals of sodium dichloroisocyanurate dihydrate are obtained under the given conditions, without loss of water of hydration occurring.

Examples of suitable water-miscible organic solvents which do not react with dichloroisocyanuric acid and can be used for carrying out the process according to the invention are methanol and acetonitrile, the use of methanol being particularly preferred. The amount of reaction medium used is calculated such that the reaction mixture remains readily stirrable and mixable throughout the entire reaction period up until removal from the reaction vessel, and that at least 2 molar equivalents of water, based on the amount of dichloroisocyanuric acid employed, are present.

Suitable basic sodium compounds for neutralization of the dichloroisocyanuric acid are, in particular, sodium hydroxide solution, sodium carbonate and, especially, sodium bicarbonate. The particular advantage in using sodium bicarbonate is that the heat of neutralization is continuously withdrawn by the evaporative cooling of the carbon dioxide escaping from the reaction, and thus no external cooling is necessary during the reaction.

In a particularly advantageous and economical embodiment of the process, the mother liquor is circulated. In this case, when the neutralization reaction has ended, the suspension is removed from the reaction vessel and separated into a solid product stream and a liquid slip stream by any known separation process. This slip stream is recycled again to the reaction vessel, in each case after addition of fresh dichloroisocyanuric acid and the equivalent amount of basic sodium compound by one of the abovementioned methods, the water content being adjusted to 20 to 30% by weight, based on the amount of organic solvent. From time to time it is necessary also to replace the amount of organic solvent entrained with the solid product. The dihydrate salt of dichloroisocyanuric acid separated off with the product stream is fed to a vacuum drier and dried under the abovementioned conditions.

Since only about 2–4% by weight of dissolved sodium dichloroisocyanurate remains in the organic mother liquor at a reaction temperature of 3° C., the mother liquor can be fed to the reaction again, without evaporation, immediately after the solid constituents have been separated off.

Even after several recyclings, no hydrolysis products or impurities which would impair the stability of the sodium dichloroisocyanurate dihydrate prepared are therefore observed in the reaction medium according to the invention.

Dichloroisocyanuric acid can be prepared as the starting material by any known process, and used for the process according to the invention.

However, it is particularly advantageous to prepare dichloroisocyanuric acid by reaction of trichloroisocyanuric acid with a water content of about 10% by weight with dry cyanuric acid in a homogenous solution directly in the reaction medium envisaged for the neutralization. In this manner, the water balance in the mother liquor is correctly maintained by addition of in each case fresh water-containing trichloroisocyanuric acid when each reaction cycle has ended.

The product of the process according to the invention, i.e. sodium dichloroisocyanurate dihydrate, is obtained in the form of coarse, very free-flowing crystals, and has excellent storage stability and free-flowing properties. Compared with the conventional processes, the process according to the invention has the advantage that the reaction medium can be re-used without being worked up and without the quality of the sodium dichloroisocyanurate dihydrate prepared thereby being reduced, and that the product can be dried simply and quickly without water of hydration being split off.

The examples which follow are intended to illustrate the process according to the invention:

EXAMPLE 1

99 g of dichloroisocyanuric acid are suspended in a mixture of 500 g of methanol and 100 g of water and the suspension is cooled to 3° C. 40 g of 50% strength aqueous NaOH solution are added in the course of 45 minutes, while stirring. When the addition of alkali has ended, stirring is continued at 3° C. for a further 15 minutes, whereupon coarsely crystalline sodium dichloroisocyanurate dihydrate precipitates. The crystalline product (110 g) is separated off by centrifugation and then freed from the solvent by drying at 35° C. under a water pump vacuum for 2 hours. 102 g of coarsely crystalline, very free-flowing sodium dichloroisocyanurate dihydrate are thus obtained. A further 79 g of dichloroisocyanuric acid are suspended in the filtrate, and 32 g of 50% strength aqueous NaOH solution are added. When neutralization, separation and drying are complete, a further 102 g of sodium dichloroisocyanurate dihydrate are obtained, with a water content of 14.0% by weight and an available chlorine content of 55.4%, corresponding to a yield of 100%.

EXAMPLE 2

50 g of dichloroisocyanuric acid are suspended in 500 g of a solution, saturated at 25° C., of sodium dichloroisocyanurate in a methanol/water mixture which originates from an earlier reaction and has a water content of 30% by weight, based on the amount of methanol, and 13.4 g of solid sodium carbonate are added at 5° C., while stirring. After 60 minutes, the crystalline solid (70 g) is filtered off and dried at 30° C. under a water pump vacuum for 3 hours. 64 g of sodium dichloroisocyanurate dihydrate are obtained in this manner as a coarsely crystalline, free-flowing loose material.

EXAMPLE 3

50 g of dichloroisocyanuric acid are introduced into 500 g of a saturated solution of sodium dichloroisocyanurate in acetonitrile/$H_2O$ (80:20) at 10° C., and 21.2 g of solid sodium bicarbonate are added. The reaction mixture is stirred for 2 hours, without further external cooling, in order to bring the crystallization to completion, and the precipitate which has deposited is separated off and dried at 35° C. in vacuo for 3.5 hours. 64 g of sodium dichloroisocyanurate dihydrate of good crystalline quality are thus obtained.

EXAMPLE 4

33.6 g of sodium bicarbonate are added in portions, while stirring, to a reaction mixture which contains dichloroisocyanuric acid and is formed by suspending, with substantial solution, 69 g of moist trichloroisocyanuric acid with a water content of 10.4% by weight and 17.2 g of dry cyanuric acid in 600 g of a methanol/water mixture (5:1), saturated with sodium dichloroisocyanurate, at 5° C. and thoroughly mixing the components. After a reaction time of 2 hours, the solid product is separated off, introduced into a vacuum drier and dried at 25° C. for 4 hours. 101 g of sodium dichloroisocyanurate dihydrate of coarsely crystalline quality and with free-flowing properties are obtained in this manner.

The liquid slip stream is supplemented by addition of 7 g of a methanol/water mixture (5:1) and recycled to the reaction vessel. After addition of 69 g of trichloroisocyanuric acid with a water content of 10% by weight and 17.2 g of dry cyanuric acid, sodium bicarbonate is added under the abovementioned conditions, until neutralization has occurred. When this procedure is repeated 10 times, in each case 100 to 103 g of sodium dichloroisocyanurate dihydrate of constantly good crystallinity and purity are obtained in each reaction cycle.

What I claim is:

1. A process for the preparation of coarsely crystalline, free-flowing sodium dichloroisocyanurate dihydrate, which comprises reacting dichloroisocyanuric acid with the equivalent amount of a base from the group of sodium hydroxide, sodium carbonate and sodium bicarbonate at temperatures from 0° C. to room temperature in a reaction medium which contains 20 to 30 parts by weight of water per 70 to 80 parts by weight of an organic, water-miscible solvent which is inert towards dichloroisocyanuric acid and is used in an amount such that at least 2 molar equivalents of water, based on the amount of dichloroisocyanuric acid employed, are present, and then separating off the sodium dichloroisocyanurate dihydrate, which is obtained in a coarsely crystalline form, and removing the organic solvent, together with free water still adhering, by drying in vacuo at room temperature to 50° C.

2. The process as claimed in claim 1, wherein the dichloroisocyanuric acid is dissolved or suspended in the reaction medium and the equivalent amount of basic sodium compound is added, with stirring.

3. The process as claimed in claim 1, wherein the dichloroisocyanuric acid is dissolved in the organic solvent, which is part of the reaction medium, and reacted with an aqueous solution of the basic sodium compound, the concentration of which is calculated such that the water content of the reaction mixture is at least 20 and at most 30 parts by weight per 100 parts by weight of reaction medium at the neutralization point.

4. The process as claimed in claim 1, wherein the reaction is carried out in a reaction medium containing 20 to 25 parts by weight of water per 100 parts by weight.

5. The process as claimed in claim 1, wherein the reaction is carried out at a temperature of 0° to 5° C.

6. The process as claimed in claim 1, wherein methanol is used as the organic solvent.

7. The process as claimed in claim 1, wherein sodium bicarbonate is used for neutralizing the dichloroisocyanuric acid.

8. The process as claimed in claim 1, wherein, when the reaction has ended, the suspension is removed from the reaction vessel and separated into a solid product stream and a liquid slip stream, after which the latter is recycled to the reaction vessel, equivalent amounts of the reactants being added and the water content being adjusted to 20 to 30 parts by weight per 100 parts by weight of reaction medium.

* * * * *